United States Patent [19]

Böhner et al.

[11] 4,350,521
[45] Sep. 21, 1982

[54] HERBICIDAL α-[4-(3',5'-DICHLOROPYRID-2'-YL)-OXY]-PHENOXY-PROPIONIC ACID γ-BUTYROLACTONE ESTER AND THIOESTER

[75] Inventors: Beat Böhner, Binningen; Hermann Rempfler, Ettingen, both of Switzerland

[73] Assignee: Ciba-Geigy Corporation, Ardsley, N.Y.

[21] Appl. No.: 241,808

[22] Filed: Mar. 9, 1981

Related U.S. Application Data

[62] Division of Ser. No. 106,797, Dec. 26, 1979, Pat. No. 4,284,566.

[30]   Foreign Application Priority Data

Jan. 4, 1979 [CH] Switzerland ............................ 52/79

[51] Int. Cl.³ .................... A01N 43/40; C07D 239/72
[52] U.S. Cl. ........................................ 71/94; 546/283
[58] Field of Search ...................... 71/88, 94; 546/283; 260/343.6

[56]         References Cited
         U.S. PATENT DOCUMENTS 4,133,675  1/1979  Schurter et al. .................. 546/283

OTHER PUBLICATIONS

Nishiyama et al, "Glycidyl Esters of, etc.;" (1979) CA 91, No. 39296e, (1979).
I.C.I., "Substituted Carbamoyl Ders." (1965), CA 66, No. 55369v., (1967).

Primary Examiner—Glennon H. Hollrah
Attorney, Agent, or Firm—Frederick H. Rabin

[57]           ABSTRACT

The novel α-phenoxy-propionic acid-γ-butyrolactone esters and thioesters of the formula

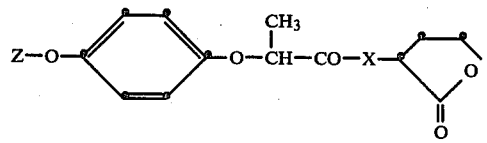

wherein
  X is oxygen or sulfur, and
  Z is the 4-trifluoromethylphenyl group or the 3,5-dichloropyridyl-2 group, have a herbicidal action. They are particularly suitable for selectively controlling gramineous weeds in cultivated crops.

5 Claims, No Drawings

HERBICIDAL α-[4-(3',5'-DICHLOROPYRID-2'-YL)-OXY]-PHENOXY-PROPIONIC ACID γ-BUTYROLACTONE ESTER AND THIOESTER

This is a divisional of application Ser. No. 106,797 filed on Dec. 26, 1979 now U.S. Pat. 4,284,566.

The present invention relates to novel α-phenoxypropionic acid-γ-butyrolactone esters and thioesters having a herbicidal action, to processes for producing them, to compositions containing them as active substances, as well as to the use thereof for controlling undesirable plant growth.

The α-phenoxy-propionic acid-γ-butyrolactone esters and thioesters correspond to the formula I

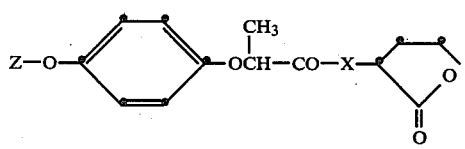

wherein

X is oxygen or sulfur, and

Z is the 4-trifluoromethylphenyl group or the 3,5-dichloropyridyl-2 group.

Phenoxy-phenoxy-alkanecarboxylic acid-γ-butyrolactone esters having a herbicidal action are described in the German Offenlegungsschrift No. 2,804,074.

The compounds of the present application are novel and they surprisingly have an excellent herbicidal activity, which is not achieved by the esters of the German Offenlegungsschrift No. 2,804,074, and they have interesting selectivity with respect to individual cultivated plants, for example soya bean plants.

The compounds have low toxicity for humans and animals. No special precautionary measures are required for the handling of these compounds. They are applied in the field advantageously in amounts of 5 kg/hectare and less. They can be used in the pre-emergence process, but application is carried out preferably after emergence of the cultivated plants.

The α-phenoxy-propionic acid-γ-butyrolactone esters and thioesters of the formula I are produced in a manner known per se by reacting α-[4-(p-trifluoromethylphenoxy)-phenoxy)-propionic or thiopropionic acid or α-[4-(3',5'-dichloropyridyl-2'-oxy)-phenoxy]-propionic or thiopropionic acid of the formula II

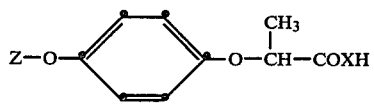

wherein X and Z have the meanings given under the formula I, with α-bromo-γ-butyrolactone of the formula III

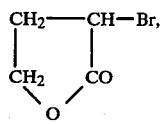

in an inert solvent, in the presence of an acid-binding agent.

The α-phenoxy-propionic and thiopropionic acids required as starting products of the formula II are known. The production thereof is described for example in the following publications: German Offenlegungsschriften Nos. 2,531,643 and 2,546,251, G.B. Patent Specification No. 1,507,643, U.S. Patent Specification No. 4,046,553 and Swiss Patent Application No. 14398/77. α-Bromo-γ-butyrolactone is obtainable commercially.

The following Examples illustrate the production of the compounds according to the invention. Temperatures are given in degrees Centigrade, and parts and percentage values relate to weight.

EXAMPLE 1

2-[4-(4-Trifluoromethylphenoxy)-phenoxy]-propionic acid-2-γ-butyrolactone ester

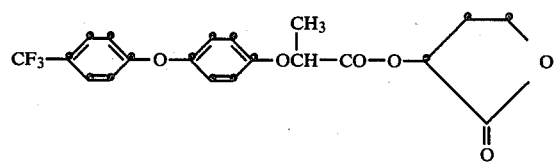

16.3 g (0.05 mol) of 2-[4-(4-trifluoromethylphenoxy)-phenoxy]-propionic acid is dissolved in 30 ml of acetone, and 8.2 g (0.06 mol) of potassium carbonate is added. The mixture is stirred at 40° for 1 hour, and 4.9 ml (0.052 mol) of α-bromo-γ-butyrolactone is added. After 2 hours' stirring at 40°, the reaction mixture is filtered, and the filtrate is concentrated by evaporation. It is then dissolved in a small amount of carbon tetrachloride, and the solution is treated with active charcoal. Concentration by evaporation leaves a clea brown oil. The yield is 18.8 g (91.7% of theory) of the above-stated ester, which has the refractive index $n_D^{22} = 1.5213$.

EXAMPLE 2

2-[4-(4-Trifluoromethylphenoxy)-phenoxy]-thiopropionic acid-S-2-γ-butyrolactone ester

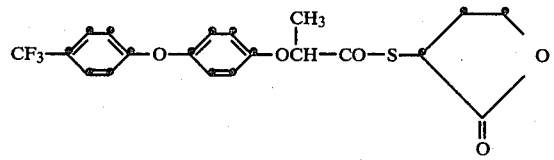

17.1 g (0.05 mol) of 2-(4-(4-trifluoromethylphenoxy)-phenoxy-propionthiolic acid is dissolved in 30 ml of acetone, and 8.2 g (0.06 mol) of potassium carbonate is added. The reaction proceeds slightly exothermically. Stirring is maintained for 30 minutes at 40°. There is then added dropwise at room temperature 4.9 ml (0.052 mol) of α-bromo-γ-butyrolactone, which results in a moderately exothermic reaction. After 10 minutes at 40°, the mixture is filtered, and the filtrate is concentrated by evaporation to leave a black viscous substance. This is dissolved in a small amount of carbon tetrachloride, and the solution is treated with active charcoal. After filtration and concentration by evaporation of the filtrate, the product obtained is in the form of a clear light-yellow viscous oil, which is pure in the thin-layer chromatogram. This yield is 17.4 g (81.7% of theory) of the above ester, which has a refractive index $n_D^{22} = 1.5341$.

EXAMPLE 3

2-[4-(3',5'-Dichloropyridyl-2'-oxy)-phenoxy]-propionic acid-2-γ-butyrolactone ester

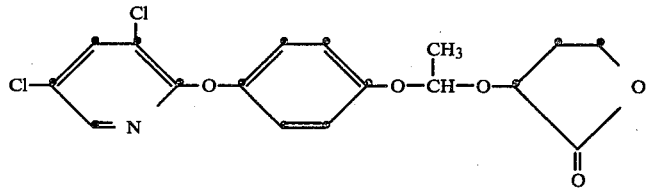

16.4 g (0.05 mol) of 2-(4-(3',5'-dichloropyridyl-2'-oxy)-phenoxy)-propionic acid is dissolved in 30 ml of acetone, and 8.2 g (0.06 mol) of potassium carbonate is added. The mixture is stirred for 10 minutes at 40°, and at room temperature there is added dropwise 4.9 ml (0.052 mol) of α-bromo-γ-butyrolactone. The reaction mixture is stirred for 1 hour at 40°, and subsequently filtered. The filtrate is treated with active charcoal and is then concentrated by evaporation to leave as residue a clear light-yellow, slightly viscous oil; this appears pure in the thin-layer chromatogram and has the refractive index $n_D^{22} = 1.5549$. The yield is 17.9 g (86.9% of theory).

EXAMPLE 4

2-[4-(3',5'-Dichloropyridyl-2'-oxy)-phenoxy]-thiopropionic acid-S-2-γ-butyrolactone ester

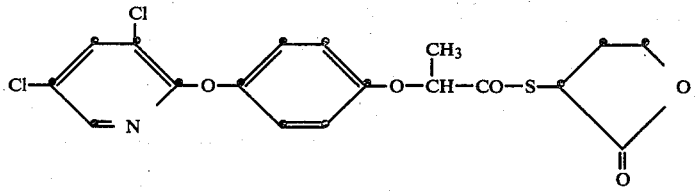

17.2 g (0.05 mol) of 2-(4-(3',5'-dichloropyridyl-2'-oxy)-phenoxy)-propionthiolic acid is dissolved in 30 ml of acetone, and 8.2 g (0.055 mol) of potassium carbonate is added. The reaction is slightly exothermic (32°). Stirring is maintained for 30 minutes at 40°, and 4.9 ml (0.052 mol) of α-bromo-γ-butyrolactone is then added dropwise, which results in a moderately exothermic reaction. The reaction mixture is stirred for 30 minutes at 40°, and becomes a bluish-green suspension. This is filtered through Hyflo and, after concentration by evaporation, there remains a black substance. This is dissolved in a small amount of carbon tetrachloride, whereupon black flakes precipitate out. These are filtered off, and the filtrate is concentrated by evaporation to leave a light-yellow clear, slightly viscous residue. The yield is 17.0 g (79.4% of theory), which appears pure in the thin-layer chromatogram, and has a refractive index of $n_D^{22} = 1.5840$.

The novel α-phenoxy-propionic acid-oxofuryl esters and thioesters of the formula I, as well as the compositions containing them, have, even when the amounts applied are small, an excellent selective herbicidal action against weeds in various cultivated crops, especially in dicotyledonous cultivated crops.

A preferred field of application is for example the controlling of gramineous weeds in cultivated crops, such as cotton, sugar beet, soya bean and vegetable crops.

Although the novel active substances of the formula I are effective in the case both of pre-emergence and of post-emergence application, post-emergence application as contact herbicides appears to deserve preference, although pre-emergence-application too is of interest.

The novel active substances are preferably formulated for example as 25% wettable powders, or for example as 20% emulsifiable concentrates and, diluted with water, applied after emergence of the cultivated crops.

Herbicidal action with application of the active substances after emergence of the plants (post-emergence).

Various cultivated plants and weeds are grown from the seeds in small pots in a greenhouse until they have reached the 4- to 6-leaf stage. The plants are then sprayed with aqueous active-substance emulsions (obtained from a 20% emulsifiable concentrate) in varying dosages. The plants are then kept under optimum conditions with regard to light, watering and temperature (22°–25° C., relative humidity 50–70%) An evaluation of the test results is made 15 days after treatment, the following scale of ratings being taken as a basis:

1 plant has died off,
2–8 intermediate stages of damage,
9 plant has flourished as in the case of the untreated control plant.

The compounds of the present invention are compared in this test with 2-[4-(4-chlorophenoxy)-phenoxy]-propionic acid-2-γ-butyrolactone ester=compound A, known from German Offenlegungsschrift No. 2,804,074, Example 48. The results are recorded in the following Table

| Compound tested amount applied in kg/hectare | Example 1 | Example 2 | Example 3 | Example 4 | Example A |
|---|---|---|---|---|---|
| plant | 2 1 ½ ¼ | 2 1 ½ ¼ | 2 1 ½ ¼ | 2 1 ½ ¼ | 2 1 ½ ¼ |

| Compound tested amount applied in kg/hectare | Example 1 2 1 ½ ¼ ⅛ | Example 2 2 1 ½ ¼ ⅛ | Example 3 2 1 ½ ¼ ⅛ | Example 4 2 1 ½ ¼ ⅛ | Example A 2 1 ½ ¼ ⅛ |
| --- | --- | --- | --- | --- | --- |
| soya bean | 7 8 9 9 9 | 7 9 9 9 9 | 7 8 9 9 9 | 5 8 9 9 9 | 9 9 9 9 9 |
| avena fatua | 1 1 3 9 9 | 2 2 6 9 9 | 1 1 1 3 3 | 1 1 2 4 4 | 9 9 9 9 9 |
| lolium perenne | 2 3 4 6 9 | 2 3 4 4 9 | 2 3 3 6 7 | 2 2 3 3 8 | 4 6 6 9 9 |
| alopecurus myosuroides | 2 2 5 6 9 | 2 3 3 6 7 | 2 2 3 3 4 | 2 2 3 3 4 | 2 2 6 7 9 |
| digitaria sanguinalis | 1 1 1 2 2 | 1 1 1 2 2 | 1 1 1 1 1 | 1 1 1 2 2 | 1 2 3 3 4 |
| sorghum halepense | 1 1 1 1 5 | 1 1 1 1 2 | 1 1 1 1 1 | 1 1 1 1 1 | 7 9 9 9 9 |
| rottboellia exaltata | 1 1 2 4 9 | 1 2 2 3 9 | 1 1 1 1 3 | 1 1 1 1 6 | 6 8 9 9 9 |

The novel active substances of the formula I are stable compounds which are soluble in customary organic solvents, such as alcohols, ethers, ketones, dimethylformamide, dimethyl sulfoxide, and so forth.

The compositions according to the invention are produced in a manner known per se by the intimate mixing and grinding of active substances of the general formula I with suitable carriers and/or distributing agents, optionally with the addition of antifoaming agents, wetting agents, dispersing agents and/or solvents, all inert to the active substances. The active substances can be obtained and used in the following forms:
 solid preparations: dusts, scattering agents, granules, (coated granules, impregnated granules and homogeneous granules);
 water-dispersible concentrates of active substance: wettable powders, pastes, emulsions and emulsion concentrates; and
 liquid preparations: solutions.

The concentration of active substance in the compositions according to the invention is 1 to 80 percent by weight, and when being applied the compositions can if necessary contain the active substances also at a lower concentration, such as about 0.05 to 1 percent by weight.

Other biocidal active substances or compositions can be mixed with the described compositions according to the invention.

The following formulation examples are intended to further illustrate the production of solid and liquid preparations.

Emulsion concentrate

The following constituents are mixed together to produce a 25% emulsion concentrate:
 25 parts of an active substance of the formula I,
 5 parts of a mixture of nonylphenolpolyoxyethylene or calcium dodecylbenzene sulfate,
 15 parts of cyclohexanone, and
 55 parts of xylene.

This concentrate can be diluted with water to give emulsions of suitable concentration, for example 0.1 to 10%; emulsions of this type are suitable for controlling weeds in crops of cultivated plants.

Granulate

The following substances are used to produce a 5% granulate:
 5 parts of one of the active substances of the formula I,
 0.25 part of epichlorohydrin,
 0.25 part of cetyl polyglycol ether,
 3.50 parts of polyethylene glycol, and
 91 parts of kaolin (particle size: 0.3-0.8 mm).

The active substance is mixed with epichlorohydrin, and dissolved in 6 parts of acetone; polyethylene glycol and cetyl polyglycol ether are then added. The solution thus obtained is sprayed onto kaolin, and the acetone is subsequently evaporated off in vacuo.

Wettable powder

The following constituents are used to produce (a) a 70% wettable powder and (b) a 10% wettable powder:

(a)

70 parts of an active substance of the formula I,
 5 parts of sodium dibutyl-naphthalene sulfonate,
 3 parts of naphthalenesulfonic acid/phenolsulfonic acid/formaldehyde condensate (3:2:1),
 10 parts of kaolin, and
 12 parts of Champagne chalk; and (b)

10 parts of an active substance of the formula I,
 3 parts of a mixture of the sodium salts of saturated fatty alcohol sulfates,
 5 parts of naphthalenesulfonic acid/formaldehyde condensate, and
 82 parts of kaolin.

The given active substance is absorbed onto the appropriate carriers (kaolin and chalk), and the material is subsequently mixed and ground with the remaining constituents. Wettable powders having excellent wetting and suspension properties are obtained. It is possible to obtain from wettable powders of this type, by dilution with water, suspensions containing 0.1 to 80% of active substance, and these suspensions are suitable for controlling weeds in crops of cultivated plants.

Paste

The following substances are used to produce a 45% paste:
 45 parts of an active substance of the formula I,
 5 parts of sodium aluminium silicate,
 14 parts of cetyl polyglycol ether having 8 mols of ethylene oxide,
 1 part of oleyl polyglycol ether having 5 mols of ethylene oxide,
 2 parts of spindle oil,
 10 parts of polyethylene glycol, and
 23 parts of water.

The active substance is intimately mixed and ground with the additives in apparatus suitable for the purpose. There is obtained a paste from which can be produced, by dilution with water, suspensions of any desired concentration.

What is claimed is:

1. An α-phenoxy-propionic acid-γ-butyrolactone ester or thioester of the formula I

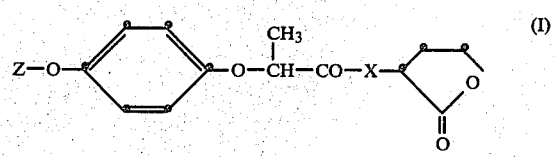

wherein

X is oxygen or sulfur,

Z is the 3,5-dichloropyridyl-2 group.

2. As compound according to claim 1 2-[4-(3',5'-dichloropyridyl-2'-oxy)-phenoxy]-propionic acid-2-γ-butyrolactone ester.

3. As compound according to claim 1 2-[4-(3',5'-dichloropyridyl-2'-oxy)-phenoxy]-thiopropionic acid-S-2-γ-butyrolactone ester.

4. A herbicidal composition which contains as active substance an effective amount of an α-phenoxy-propionic acid-oxofuryl ester or thioester of the formula I, claim 1, together with inert constituents.

5. A method for controlling undesirable growth in cultures of cultivated crops which comprises applying to said cultures a herbicidally effective amount of a compound of the formula

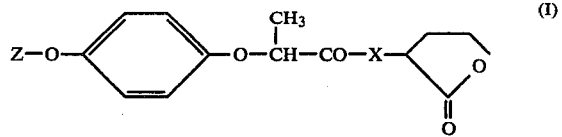

wherein X is oxygen or sulfur, and Z is 3,5-dichloropyridyl-2.

* * * * *